(12) United States Patent
Pawlowicz, III

(10) Patent No.: US 7,844,340 B2
(45) Date of Patent: Nov. 30, 2010

(54) DEVICES AND METHODS FOR TRANSCUTANEOUS ELECTRICAL NEURAL STIMULATION

(76) Inventor: John S. Pawlowicz, III, 638 E. Village Green Blvd., Mars, PA (US) 16046

(*) Notice: Subject to any disclaimer, the term of this patent is extended or adjusted under 35 U.S.C. 154(b) by 157 days.

(21) Appl. No.: 12/023,117

(22) Filed: Jan. 31, 2008

(65) Prior Publication Data

US 2008/0215113 A1 Sep. 4, 2008

Related U.S. Application Data

(60) Provisional application No. 60/898,629, filed on Jan. 31, 2007.

(51) Int. Cl.
*A61N 1/00* (2006.01)
(52) U.S. Cl. .................................................. 607/46
(58) Field of Classification Search ............... 600/509; 607/2, 42, 46, 48, 49, 61, 60
See application file for complete search history.

(56) References Cited

U.S. PATENT DOCUMENTS

| | | | |
|---|---|---|---|
| 3,593,422 A | 7/1971 | Jankelson | |
| 3,797,500 A | 3/1974 | Porter | |
| 3,983,881 A | 10/1976 | Wickham | |
| 4,084,595 A | 4/1978 | Miller | |
| 4,174,706 A | 11/1979 | Jankelson et al. | |
| 4,342,086 A | 7/1982 | Adib | |
| 4,344,441 A | 8/1982 | Radke | |
| 4,386,614 A | 6/1983 | Ryan | |
| 4,459,109 A | 7/1984 | Radke | |
| 4,553,549 A | 11/1985 | Pope et al. | |
| 4,586,509 A | 5/1986 | Liss et al. | |
| 4,595,010 A * | 6/1986 | Radke | 607/74 |
| 4,765,345 A | 8/1988 | Adib | |
| 4,782,837 A | 11/1988 | Hogan | |
| 4,786,277 A | 11/1988 | Powers et al. | |
| 4,836,778 A | 6/1989 | Baumrind et al. | |

(Continued)

FOREIGN PATENT DOCUMENTS

EP 797972 10/1997

(Continued)

OTHER PUBLICATIONS

Matheson et al., "EMG Scanning normative data", J of Psychopathology and Behavioral Assessment, vol. 10, No. 1, pp. 9-20, 1988, Abstract.

(Continued)

*Primary Examiner*—George Manuel
*Assistant Examiner*—Robert N Wieland
(74) *Attorney, Agent, or Firm*—Calfee, Halter & Griswold LLP

(57) ABSTRACT

In an inventive method of performing transcutaneous electrical neural stimulation on a human patient, first and second input electrodes are secured over left and right trapezius muscle regions of the patient. Third and fourth input electrodes are secured over left and right posterior cervical and suboccipital muscle regions of the patient. Fifth and sixth input electrodes are secured over left and right preauricular areas of the patient. A first electrical current is supplied to each of the first and second electrodes. A second electrical current is supplied to each of the third and fourth electrodes. A third electrical current is supplied to each of the fifth and sixth electrodes.

20 Claims, 3 Drawing Sheets

U.S. PATENT DOCUMENTS

| | | | |
|---|---|---|---|
| 4,837,685 A | 6/1989 | Jokela | |
| 5,513,651 A | 5/1996 | Cusimano et al. | |
| 5,662,118 A | 9/1997 | Skubick | |
| 6,023,642 A | 2/2000 | Shealy et al. | |
| 6,058,938 A | 5/2000 | Chu et al. | |
| 2003/0045922 A1 | 3/2003 | Northrup | |
| 2003/0130709 A1 | 7/2003 | D.C. et al. | |
| 2003/0135129 A1 | 7/2003 | Cusimano et al. | |
| 2004/0044338 A1* | 3/2004 | Lennox et al. | 606/32 |
| 2004/0088025 A1 | 5/2004 | Gesotti | |
| 2004/0158297 A1 | 8/2004 | Gonzalez | |
| 2004/0236383 A1 | 11/2004 | Yelizarov | |
| 2005/0021103 A1 | 1/2005 | DiLorenzo | |
| 2006/0047325 A1 | 3/2006 | Thimineur et al. | |
| 2006/0089683 A1* | 4/2006 | Hagglof et al. | 607/48 |
| 2006/0136008 A1 | 6/2006 | Tadlock | |
| 2006/0149337 A1* | 7/2006 | John | 607/45 |

FOREIGN PATENT DOCUMENTS

| | | |
|---|---|---|
| WO | 97/13454 | 4/1997 |
| WO | 99/37223 | 7/1999 |
| WO | 2004/056419 | 7/2004 |
| WO | 2005/062829 | 7/2005 |
| WO | 2006/014896 | 2/2006 |

OTHER PUBLICATIONS

Thomas et al., "Relationship of masseter electromyographic activity to mandible position in the freeley-moving rat", Archives of Oral Biology, vol. 28, No. 11, pp. 1043-6, 1983, Abstract.

Murphy, "Electrotherapeutics in the Clinical Management of Head, Neck, Facial Pain and Temporomandibular Joint Disorders", Anthology of Craniomandibular Orthopedics, vol. II, pp. 41-85, Dec. 1992.

Cooper et al., "Electromyography of Masticatory Muscles in Craniomandibular Disorders", Anthology of Craniomandibular Orthopedics, vol. II, pp. 127-143, Dec. 1992.

Lynn, "Correlation of Resting and Functional EMG and 17 Sites of Pain in the Head and Neck Region", Anthology of Craniomandibular Orthopedics, vol. II, pp. 145-158, Dec. 1992.

Winber et al., "Surface Electrode Electromyography in the Diagnosis, Quantification, and Documentation of Craniomandibular Disorders", Anthology of Craniomandibular Orthopedics, vol. II, pp. 159-169, Dec. 1992.

Simmons, "Neuromuscular Orthotics in the Treatment of Bruxing and Clenching in Subjects with and without Cervical Pathology", pp. 141-148, The Application of the Principles of Neuromuscular Dentistry to Clinical Practice, received by facsimile on Jan. 26, 2007.

Losert-Burggner et al., "Snoring Splints as Therapy for Cranio-Mandibular and Cranio-Cervical Dysfunctions", pp. 125-139, The Application of the Principles of Neuromuscular Dentistry to Clinical Practice, received by facsimile on Jan. 26, 2007.

Eatmon, "The History of the International College of Craniomandibular Orthopedics", Appendix, pp. 149-152, 2005, The Application of the Principles of Neuromuscular Dentistry to Clinical Practice, received by facsimile on Jan. 26, 2007.

The Benefits of TENS in Dentistry, Answers to Frequently Asked Questions About the Use and Benefits of TENS in Dentistry, brochure, Myotronics-Noromed, Inc. Jun. 2005, TM5M.

K7/EMG Eight Channel Electromyograph, one page web printout dated Jun. 6, 2006, http://www.myotronics.com/NR/store/index.cfm?action=cat.prodInfo&partNo=k7_emg.

Brochure "Now! Relax Cervical & Masticatory Muscles Simultaneously! The J5 Myo-monitor, Ultra-low Frequency Electrical Muscle Simulator", Myotronics, 2005, 2 pgs.

Brochure, "K7 Evaluation System, The Comprehensive Instrument for Precise Occlusal Evaluation", Myotronics, Mar. 2003, 4 pgs.

Web pages, Neuromuscular Dentistry for 25 years Dr. Bill Williams Suwanee, Georgia, printed Jun. 6, 2006 from http://www.suwaneedental.com/neuromuscular.html, 7 pgs.

Brochure, "Frequently asked questions about Neuromuscular Dentistry", Jan. 2004, Myotronics.

Brochure, "Neuromuscular Dentistry", Myotronics-Noromed, Inc., Nov. 2002.

Neuromuscular Dental Diagnosis and Treatment, published 1st ed. 1990, 2nd ed. 2005, pp. 58-60, 68-69 and 73-81, received by facsimile on Jan. 22, 2007.

Article by Norman Thomas, "Neuromuscularocclusion", pp. 32-40, Jan./Feb./Mar. 2006, LVI Visions magazine.

Ciuffolo et al., "Surface electromyographic response of the neck muscles to maximal voluntary clenching of the teeth", J of Oral Rehabilitation, vol. 32, No. 2, pp. 79-84, Feb. 2005, Abstract.

Pallegama et al., "Influence of masticatory muscle pain on electromyographic activities of cervical muscles in patients with myogenous temporomandibular disorders", J of Oral Rehabilitation, vol. 31, No. 5, pp. 423-9, May 2004, Abstract.

So, et al., "Influence of occlusal contact on cervical muscle activity during submaximal clenching", J of Oral Rehab., vol. 31, No. 5, pp. 417-422, May 2004, Abstract.

McKay, et al., "Electrognathographic and electromyographic observations on jaw depression during neck extension", J of Oral Rehab, vol. 26, No. 11, pp. 865-876, Nov. 1999, Abstract.

Karppinen et al., "Adjustment of dental occlusion in treatment of chronic cervicobrachial pain and headache", J of Oral Rehab, vol. 26, No. 9, pp. 715-721, Sep. 1999, Abstract.

Morrisette et al., "Sagittal plane head position and habitual posture influences on cervical muscle function (posture)", Dissertation Abstracts International, vol. 58, No. 10B, pp. 5223, 1997, Abstract.

Hsueh et al., "The immediate effectiveness of electrical nerve stimulation and electrical muscle stimulation on myofascial trigger points", Am. J of Physical Medicine & Rehab., Associate of Academic Physiatrists, vol. 76, No. 6, pp. 471-476, Nov./Dec. 1997, Abstract.

Ormeno et al., "Body position effects on sternocleidomastoid and masseter EMG pattern activity in patients undergoing occlusal splint therapy", Cranio, the J of Craniomandibular practice, vol. 15, No. 4, pp. 300-9, Oct. 1997, Abstract.

Zuniga et al., "Influence of variation in jaw posture on sternocleidomastoid and trapezius electromyographic activity", Cranio, the J of Craniomandibular practice, vol. 13, No. 3, pp. 157-162, Jul. 1995, Abstract.

Cooper et al., "Electromyography of masticatory muscles in craniomandibular disorders", The Laryngoscope, vol. 101, No. 2, pp. 150-7, Feb. 1991, Abstract.

Ferrario et al., "The influence of occlusion on jaw and neck muscle activity: a surface EMG study in healthy young adults", J of Oral Rehab., vol. 33, No. 5, pp. 341-348, May 2006, Abstract.

McLean, Linda, "The effect of postural correction on muscle activation amplitudes recorded from the cervicobrachial region", J of Electromyography and kinesiology, Official Journal of the International Society of Electrophysiological Kinesiology, vol. 15, No. 6, pp. 527-535, Dec. 2005, Abstract.

Bexander et al., "Effect of gaze direction on neck muscle activity during cervical rotation", Experimental brain research, vol. 167, No. 3, pp. 422-432, Dec. 2005, Abstract.

Valenzuela, et al., "Does head posture have a significant effect on the hyoid bone position and sternocleidomastoid electromyographic activity in young adults?", Cranio: the J of Craniomandibular practice, vol. 23, No. 3, pp. 204-211, Jul. 2005, Abstract.

Gu et al., "Feasibility of accessory nerve transportation in repairing the nerve root of cervical vertebra 5 and superior trunk of brachial plexus", Chinese J of Clinical Rehab., vol. 9, No. 25, pp. 37-39, Jul. 7, 2005, Abstract.

Falla et al., "Patients with neck pain demonstrate reduced electromyographic activity of the deep cervical flexor muscles during performance of the craniocervical flexon test", Spine, vol. 29, No. 19, pp. 2108-2114, Oct. 1, 2004 Abstract.

Kumar et al., "Cervical muscle response to posterolateral impacts—effect of head rotation", Clinical biomechanics (Bristol, Avon), vol. 19, No. 9, pp. 899-905, Nov. 2004, Abstract.

Falla et al., "Neuromuscular efficiency of the sternocleidomastoid and anterior scalene muscles in patients with chronic neck pain", Disability and rehabiliation, vol. 26, No. 12, pp. 712-717, Jun. 17, 2004, Abstract.

Audette et al., "Bilateral activation of motor unit potentials with unilateral needle stimulation of active myofascial trigger points", Am. J of Physical Medicine & Rehab./Association of Academic Physiatrists, vol. 83, No. 5, pp. 368-374, quiz 375-7, 389, May 2004 Abstract.

Falla et al., "Lack of correlation between sternocleidomastoid and scalene muscle fatigability and duration of symptoms in chronic neck pain patients", Neurophysiologie clinique=Clinical neurophysiology, vol. 34, No. 3-4, pp. 159-165, Oct. 2004, Abstract.

Falla et al., "An electromyographic analysis of the deep cervical flexor muscles in performance of craniocervical flexion", Physical therapy, vol. 83, No. 10, pp. 899-906, Oct. 2003, Abstract.

Kumar et al., "EMG power spectra of cervical muscles in lateral flexion and comparison with sagittal and oblique plane activities", European J of Applied Physiology, vol. 89, No. 3-4, pp. 367-376, May 2003, Abstract.

D'Attilio et al., "Effects of the antigravitary modification of the myotension of asset (MAGMA) therapy on myogenic cranio-cervical-mandibular dysfunction: a longitudinal surface electromyography analysis", Cranio: the J of Craniomandibular practice, vol. 21, No. 1, pp. 24-30, Jan. 2003, Abstract.

Valentino et al., "Functional correlation between the masticatory muscles and the trapezius. An EMG study", Pain Clinic, vol. 14, No. 3, pp. 251-253, 2002, Abstract.

Miralles et al., "Vertical dimension. Part 2: the changes in electrical activity of the cervical muscles upon varying the vertical dimension", Cranio: the J of Craniomandibular practice, vol. 20, No. 1, pp. 39-47, Jan. 2002, Abstract.

Santander et al., "Effects of head and neck inclination on bilateral sternocleidomastoid EMG activity in healthy subjects and in patients with myogenic cranio-cervical-mandibular dysfunction", Cranio: the J of Craniomandibular practice, vol. A 18, No. 3, pp. 181-191, Jul. 2000, Abstract.

Cram et al., "Cervical flexion: a study of dynamic surface electromyography and range of motion", J of manipulative and physiological therapeutics, vol. 22, No. 9, pp. 570-575, Nov./Dec. 1999, Abstract.

Palazzi et al., "Effects of two types of pillows on bilateral sternocleidomastoid EMG activity in healthy subjects and in patients with myogenic cranio-cervical-mandibular dyfunction", Cranio: the J of Craniomandibular practice, vol. 17, No. 3, pp. 202-212, Jul. 1999, Abstract.

Andary et al., "Neurogenic atrophy of suboccipital muscles after a cervical injury: a case study", Am. J of Physical medicine & rehabilitation/Association of Academic Physiatrists, vol. 77, No. 6, pp. 545-9, Nov./Dec. 1998, Abstract.

Sugimura et al., "Dynamic response of the monkey skull with loss of occlusal", Shika Igaku, vol. 60, No. 1, pp. 25-34, Mar. 25, 1997, Abstract.

Palazzi et al., "Body position effects on EMG activity of sternocleidomastoid and masseter muscles in patients with myogenic cranio-cervical-mandibular dysfunction", Cranio: the J of Carniomandibular practice, vol. 14, No. 3, pp. 200-209, Jul. 1996, Abstract.

Shinoda et al., "Input patterns and pathways from the six semicircular canals to motoneurons of neck muscles. I. The multifidus muscle group", J of Neurophysiology, vol. 72, No. 6, pp. 2691-2702, Dec. 1994, Abstract.

Clark et al., "Co-activation of sternocleidomastoid muscles during maximum clenching", J. of Dental Research, vol. 72, No. 11, pp. 1499-1502, Nov. 1993, Abstract.

Richmond et al., "Electromyographic studies of neck muscles in the intact cat. I. Patterns of recruitment underlying posture and movement during natural behaviors", Experimental brain research, vol. 88, No. 1, pp. 41-58, 1992, Abstract.

* cited by examiner

DEVICES AND METHODS FOR TRANSCUTANEOUS ELECTRICAL NEURAL STIMULATION

CROSS-REFERENCE TO RELATED APPLICATION

This application claims the benefit of U.S. Patent Application Ser. No. 60/898,629, entitled "DEVICES AND METHODS FOR TRANSCUTANEOUS ELECTRICAL, NEURAL STIMULATION" and filed Jan. 31, 2007, the entire contents of which are incorporated herein by reference, to the extent that they are not conflicting with the present application.

BACKGROUND

Transcutaneous Electrical Neural Stimulation (TENS) involves the application of electrical stimulation to a (usually human) subject through leads attached to electrodes in contact with the subject's skin. By electrically stimulating the nerves proximate to the placement of the electrodes, the muscles associated with the nerves may be stimulated, which may produce one or more therapeutic benefits for the subject, including, for example, muscle stimulation, muscle relaxation, or pain relief.

TENS devices may deliver electrical stimulus to a subject at a wide range of frequencies. Common TENS treatments are often classified as either high frequency TENS, with a typical frequency range of 80-100 Hz (80-100 stimuli per second) or low frequency, with a typical frequency range of 0.5-4 Hz, although frequencies outside of these ranges may also be used. High frequency TENS is often used for relieving pain by inhibiting the transmission of pain signals through neural pathways, while low frequency TENS has been found to relax and restore muscle tissue.

Many devices capable of administering TENS are known in the art. Examples of such devices are described in U.S. Pat. Nos. 3,593,422 (the "'422 patent"); 3,797,500 (the "'500 patent"); 3,983,881 (the "'881 patent"); 4,084,595 (the "'595 patent"); 4,174,706 (the "'706 patent"); 4,586,509 (the "'509 patent"); 4,595,010 (the "'010 patent"); and 6,023,642 (the "'642 patent"), the entire disclosures of which are hereby incorporated by reference in their entirety, to the extent that such disclosures are not inconsistent with the present application.

SUMMARY

The present application contemplates an inventive method of performing transcutaneous electrical neural stimulation on a human patient. First and second input electrodes are secured over left and right trapezius muscle regions of the patient. Third and fourth input electrodes are secured over left and right posterior cervical and suboccipital muscle regions of the patient. Fifth and sixth input electrodes are secured over left and right preauricular areas of the patient. A first electrical current is supplied to each of the first and second electrodes. A second electrical current is supplied to each of the third and fourth electrodes. A third electrical current is supplied to each of the fifth and sixth electrodes.

According to another inventive aspect of the present application, a device for performing transcutaneous electrical neural stimulation includes a power source, three sets of electrodes in electrical communication with the power source, a current generating mechanism, and an amplitude control mechanism. Each set of electrodes includes two input electrodes and an output electrode. The current generating mechanism is electrically connected to the power source for generating an electrical current between each of the input electrodes and the output electrode of each of the sets of electrodes. The amplitude control mechanism is configured to selectively control intensity of any one or more of the electrical currents.

DESCRIPTION OF THE DRAWINGS

Features and advantages of the invention will become apparent from the following detailed description made with reference to the accompanying drawings, wherein.

DETAILED DESCRIPTION

Figure 1:
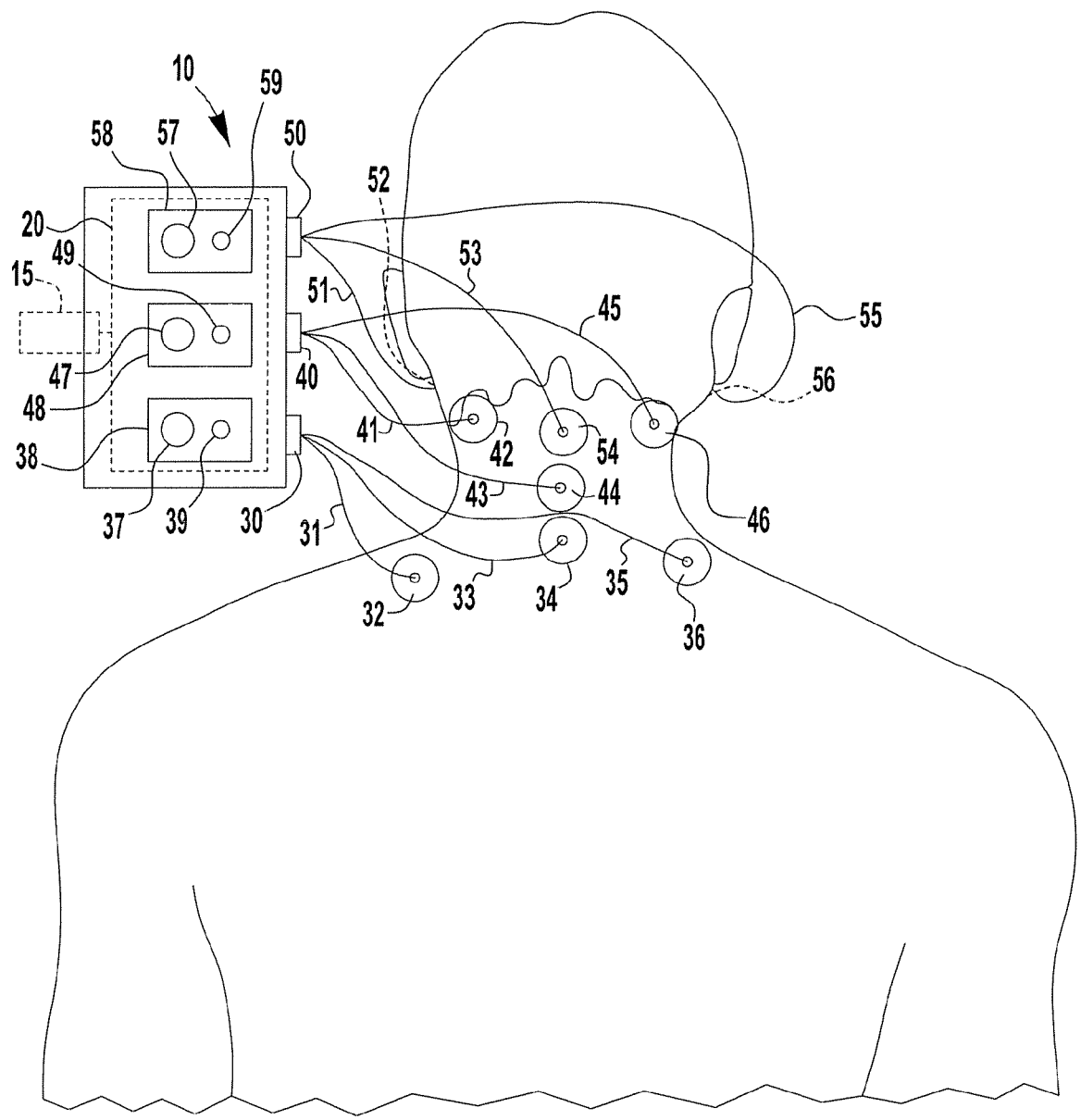
FIG. 1 illustrates an electrical stimulator device arranged for use for Transcutaneous Electrical Neural Stimulation.

This Detailed Description of the Invention merely describes embodiments of the invention and is not intended to limit the scope of the invention in any way. Indeed, the invention as described in the claims is broader than and unlimited by the preferred embodiments, and the terms used in the claims have their full ordinary meaning.

The present application is directed towards devices and methods for transcutaneous electrical neural stimulation, or TENS. In one exemplary application involving low frequency or ultra-low frequency (typically 0.67 Hz) TENS, electrical stimulation of nerve fibers that innervate the head and neck has been used in the field of dentistry to relax musculature otherwise contributing to a poor occlusion of the mandible. This relaxation of the muscles helps position the head and neck in a more neutral or balanced occlusion (or "rest position"), allowing for dental impressions and record taking of this preferred occlusion and appropriate dental treatments relating to such an occlusion. Once this rest position has been achieved, identification of the desirable muscle coordination (including duration of and intervals between muscle contractions) may be measured using an electromyograph (EMG) machine, which may facilitate in optimizing dental treatments. An example of an EMG machine for use in stimulating masticatory muscles is described in U.S. Pat. No. 4,344,441 (the "'441 patent"), the entire disclosure of which is hereby incorporated by reference. Such treatments may also provide the benefits of pain relief, such as, for example, relief of pain associated with temporomandibular disorders (TMDs) and myo-facial pain dysfunction (MPD), as repetitive muscle stimulation, in addition to relaxing the muscles, which may aid in restoring normal blood flow and removing waste products responsible for pain.

To assist in properly positioning the head and neck for improved physiologic occlusion, stimulation of both the masticatory and trapezius muscle regions (of the upper back) may be employed. These muscle groups may be stimulated sequentially or simultaneously by using a TENS device with two pairs of electrodes, which may reduce treatment time and improve efficacy. In one such application, one pair of coupled electrodes is positioned at the preauricular areas (typically over each mandibular notch), and a second pair of coupled electrodes is positioned at the trapezius muscle regions. Each coupled pair of electrodes may additionally include a third or common output electrode placed between the coupled electrodes (for example, at the nape of the neck) to provide a continuous current pathway for each electrode. This results in a bilateral condition for the pair of coupled electrodes, in which the pulsing electrical stimulus is delivered to each electrode simultaneously. This arrangement may be preferable to the use of unilateral two electrode TENS, which produces a delay between pulses at the two electrodes, and may result in inferior contraction of the musculature.

A control interface may be provided for each pair of electrodes, to control such variables as intensity/amplitude, frequency, and relative balance of stimulus intensity between the paired electrodes (which may be used, for example, to focus the electrical stimulus to one side of the musculature for acute pain relief). In some embodiments, one or more variables relating to the electrical stimulus may be fixed, or at least not adjustable by the user, for example, to ensure safe operation of the TENS device. An example of a TENS device including two sets of electrodes adapted to deliver simultaneous electrical stimulation to the masticatory and cervical muscle groups, while providing separate amplitude/intensity and balance controls for each set of electrodes (or for each muscle group) is the J5 Myo-monitor, manufactured by Myotronics-Noromed, Inc.

In performing TENS for occlusal adjustments, for example, in dental treatments, a problematic condition in patients is a head forward posture and tightness throughout the upper cervical and suboccipital regions with resultant head and neck pain. According to an inventive aspect of the present application, electrical stimulation of the suboccipital area may be utilized to relax and relieve pain from the suboccipital region, and may promote stabilization of the cervical region and prevention of muscle fatigue and resultant pain. As one example, electrical stimulation may be applied to the cervical plexus, the lesser occipital nerves C1, C2 and C3, the great auricular nerves C2 and C3, the supraclavicular nerves C3 and C4, the greater occipital nerve C2, $3^{rd}$ occipital nerve C3 and the $4^{th}$, $5^{th}$, $6^{th}$, $7^{th}$ and $8^{th}$ nerves in succession. Targeted musculature may also include the trapezius muscles and semispinalis capitus muscles, which may be the originating cause of postural, occlusal and pain difficulties in a patient. Other symptoms which may be relieved by such treatment include cardiac arrhythmia, which may be the result of a positional change of the vertebral artery, due to the muscle stress placed upon the upper cervical vertebrae in response to the need for muscle compensation and accommodation.

As one such treatment, electrical stimulation may be applied to an area known as the Suboccipital Triangle. This triangle is bounded by three suboccipital muscles and is covered by the semispinalis capitis muscle (which may be associated with the entrapment of the Greater Occipital Nerve). Exact placement of the source of electrical current (such as for example, an electrode of an electrical stimulator device) may vary from patient to patient, due to the presentation of their specific anatomical structures. As one example, placement may be in the general vicinity of the inferior pole of the Occipital bone.

According to an inventive aspect of the present application, a low frequency TENS procedure for placing the head and neck in a rest position for optimum occlusion may include additional electrical stimulation for positioning the head in a more neutral position with respect to the cervical spine. In one embodiment, an electrical stimulus is applied to the posterior cervical and suboccipital muscle regions, located between the base of the skull and the first cervical vertebra. In one example, a TENS procedure may include electrical stimulation of the posterior cervical and suboccipital muscle regions in addition to electrical stimulation of the masticatory muscles (through stimulation of the fifth and seventh cranial nerves) and/or the trapezius muscle regions of the upper back.

Many different muscles in the posterior cervical (or suboccipital) region may be targeted, including, for example, the sternocleidomastoid muscles, the rectis muscles, and the posterior cervicalis and suboccipital muscles, all located at the base of the skull and at the first cervical vertebra. In one such example, the electrodes may be placed over the Suboccipital Triangle.

This electrical stimulation may be applied sequentially; for example, stimulation of the trapezius muscle regions, then stimulation of the posterior cervical and suboccipital muscle regions (for example, for stimulation of the eleventh cranial nerve), and then stimulation of the masticatory muscles, for example, through stimulation of the fifth and seventh cranial nerves (located proximate to the preauricular areas of the jaw) to affect an occlusal adjustment. Alternatively, these regions may be stimulated simultaneously. According to another inventive aspect of the present application, in order to simultaneously stimulate the masticatory muscles and both groups or regions of trapezius and posterior cervical muscles, an electrical stimulation device may be provided with a current generating mechanism electrically connected with three (or more) sets of leads connected with electrodes, with each set of electrodes including two stimulating input electrodes (for stimulating each side of the targeted musculature) and one common electrode for completing an arc or current pathway to both stimulating electrodes. While many different types of current generating mechanisms may be used, examples include a voltage interrupter/transformer (as described, for example, in the '642 patent), a multivibrator with timing circuit (as described, for example, in the '595 patent), or an oscillator and pulse transformer (as described, for example, in the '706 patent). Since relaxation of these muscles to achieve the rest position may take 40 to 60 minutes (or longer), the ability to stimulate all three muscle groups simultaneously may save time. In addition, this simultaneous stimulation may reduce the risk of losing the benefits of stimulating a first muscle region as the second and third muscle regions are being stimulated.

In one embodiment, all three sets of electrodes are configured to deliver electrical current simultaneously at the same frequency, and may, but need not, be synchronized. Additionally or alternatively, the device may include separate controls for each set of electrodes, with each set of controls configured to allow a user to adjust one or more of the frequency, amplitude, balance, and duration of the electrical stimulation.

Figure 2:
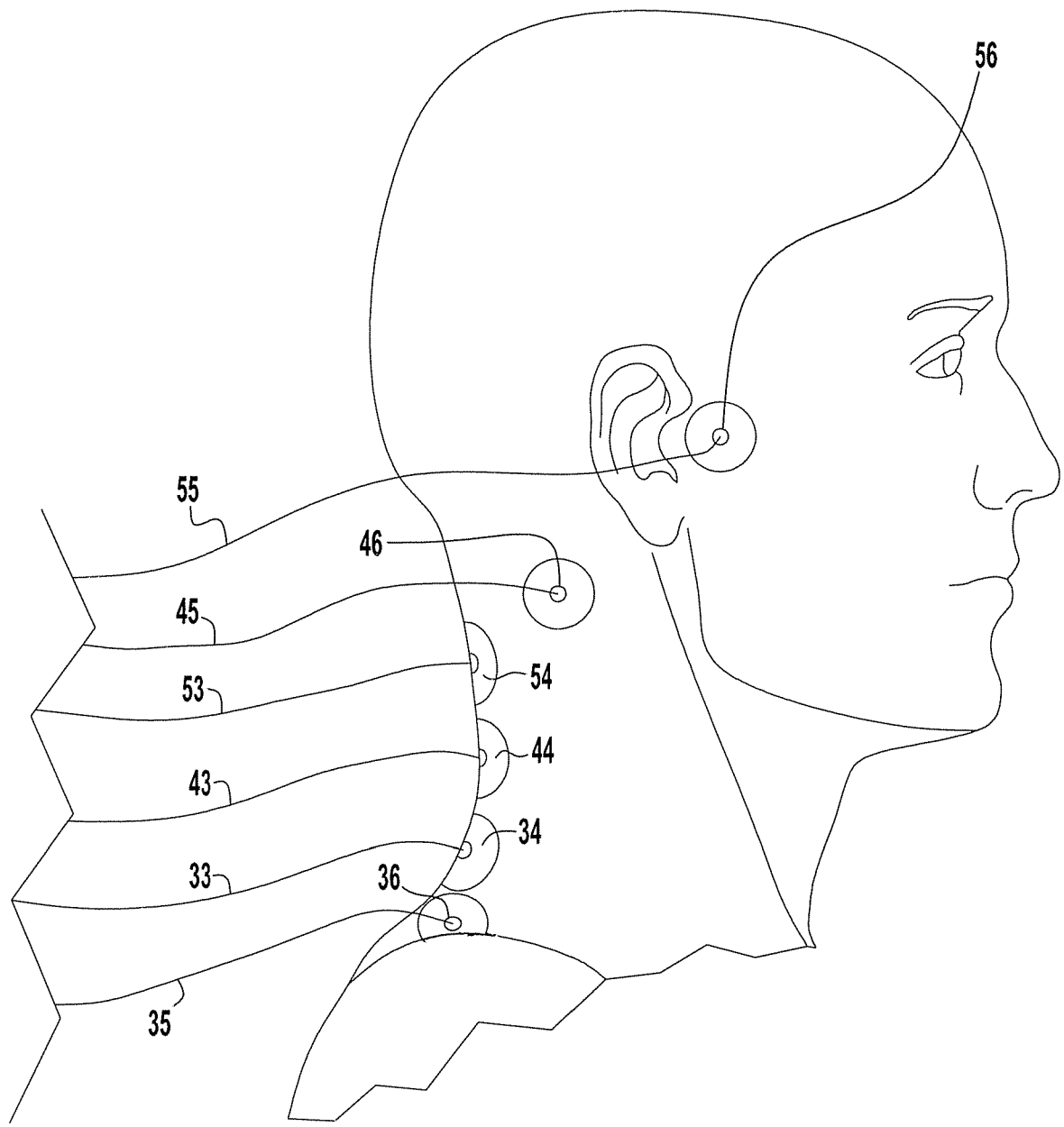
FIG. 2 illustrates another view of the electrical stimulator device of FIG. 1.

FIGS. 1 and 2 schematically illustrate the application of electrodes from an exemplary electrical stimulator device 10 according to an embodiment of the present application. The device 10 includes a power supply 15, which may be internal (e.g., a battery or batteries) or external (e.g., an electrical cord and plug) to the device enclosure. The exemplary device 10 includes three electrode sets 30, 40, 50, with each electrode set including three electrodes attached to leads. As shown, the first electrode set 30 includes first and second stimulating input electrodes 32, 36 shown attached (for example, by an adhesive) over left and right trapezius muscle regions, and a common output electrode 34 shown placed along the spine between the input electrodes 32, 36. The second electrode set 40 includes third and fourth stimulating input electrodes 42, 46, shown attached over left and right posterior cervical and suboccipital muscle regions (for example, for electrical stimulation of eleventh cranial nerve), with a common output electrode 44 shown placed along the spine between the input electrodes 42, 46. The third electrode set 50 includes fifth and sixth stimulating input electrodes 52, 56 shown attached over left and right preauricular areas above the jaw (for example, for electrical stimulation of the fifth and seventh cranial nerves to affect an occlusal adjustment), with a common electrode 54 shown placed along the spine between the input electrodes 52, 56.

The device further includes a controller or current generating mechanism 20 electrically connected with the power source 15 for delivering electrical current to the input electrodes. The circuitry of the current generating mechanism 20 may be configured to deliver simultaneous electrical pulses (with synchronized frequency) to all three sets of electrodes 30, 40, 50. While the controller may be provided with only one set of controls to control all three electrode sets, in the illustrated embodiment, each set of electrodes is provided with its own control interface 38, 48, 58, to independently control such variables as amplitude (intensity) and balance (current distribution). For example, each control interface 38, 48, 58 may include an amplitude control mechanism 37, 47, 57 (including a user operable amplitude control member, such as a knob) for selectively and separately controlling the intensity of the electrical current delivered to each electrode set. While many different amplitude control mechanisms may be utilized, one such mechanism includes a potentiometer (as described, for example, in the '642 patent). Additionally or alternatively, each control interface 38, 48, 58 may include a balance control mechanism 39, 49, 59 (including a user operable control member, such as a knob) for selectively and separately adjusting distribution of the electrical current to each of the input electrodes of each electrode set. While many different balance control mechanisms may be utilized, one such balance control is described in the '706 patent.

Figure 3:
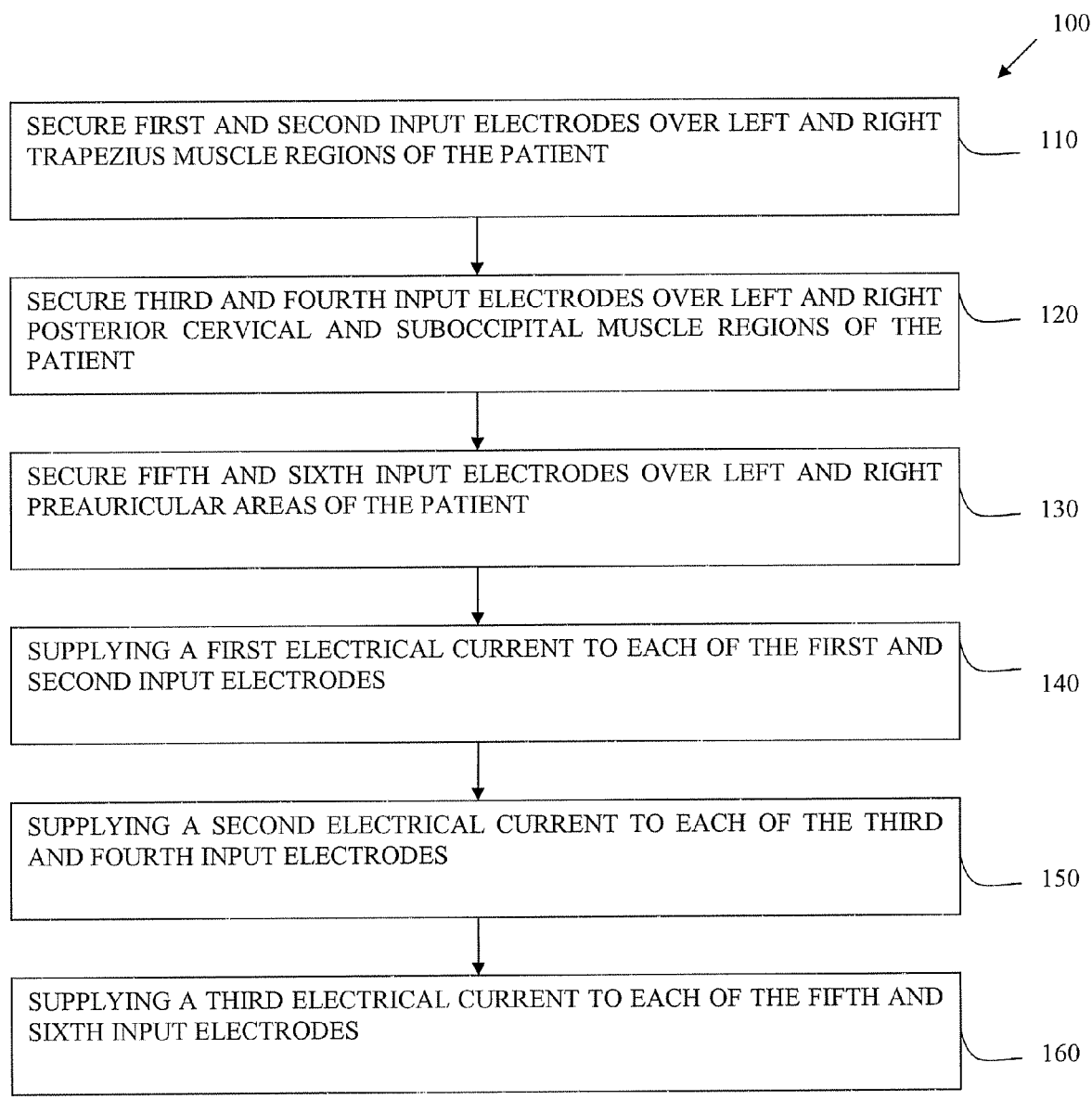
FIG. 3 schematically illustrates an exemplary method of performing transcutaneous electrical neural stimulation on a human patient.

FIG. 3 schematically illustrates an exemplary method 100 of performing transcutaneous electrical neural stimulation on a human patient. At step 110, first and second input electrodes are secured over left and right trapezius muscle regions of the patient. At step 120, third and fourth input electrodes are secured over left and right posterior cervical and suboccipital muscle regions of the patient. At step 130, fifth and sixth input electrodes are secured over left and right preauricular areas of the patient. At step 140, a first electrical current is supplied to each of the first and second input electrodes. At step 150, a second electrical current is supplied to each of the third and fourth input electrodes, for example, to affect the eleventh cranial nerve. At step 160, a third electrical current is supplied to each of the fifth and sixth input electrodes, for example, to affect the fifth and seventh cranial nerves for achieving an occlusal adjustment.

Many aspects of the TENS procedure may be adjusted, for example, to improve comfort or effectiveness. As discussed above, the intensity of each of the electrical currents may be selectively and separately adjusted, for example, as desired by the patient to increase comfort and effectiveness. The balance of distribution of each electrical current between paired input electrodes may be adjusted, for example, to relieve acute pain predominant on one side of the patient's musculature. A timer may be included to control or limit the duration of electrical stimulation. Some aspects or variables relating to the procedure may be fixed, for example, by excluding user operable controls, to maintain safe operation or effectiveness. For example, the frequency of the electrical current may be fixed at a level known to be safe and effective. As one example, transcutaneous electrical neural stimulation for occlusal adjustments of the inaudible (for example, for dental treatments) are known to be safe and effective at a frequency of approximately 0.67 Hz. As such, an electrical stimulation device may be configured to provide electrical currents at a fixed frequency of approximately 0.67 Hz.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A method of performing improved dental treatments using transcutaneous electrical neural stimulation on a human patient, the method comprising:
   securing a first input electrode over a left trapezius muscle region of the patient;
   securing a second input electrode over a right trapezius muscle region of the patient;
   securing a third input electrode over a left posterior cervical and suboccipital muscle region of the patient;
   securing a fourth input electrode over a right posterior cervical and suboccipital muscle region of the patient;
   securing a fifth input electrode over a left preauricular area of the patient;
   securing a sixth input electrode over a right preauricular area of the patient;
   supplying a first electrical current to each of the first and second electrodes;
   supplying a second electrical current to each of the third and fourth electrodes;
   supplying a third electrical current to each of the fifth and sixth electrodes; and
   measuring an occlusion resulting from the first, second, and third supplied electrical currents to verify a desired head and neck rest position of the patient.

2. The method of claim 1, wherein the first, second, and third electrical currents are each at substantially the same frequency.

3. The method of claim 1, wherein frequencies of the first, second, and third electrical currents are synchronized.

4. The method of claim 1, wherein the first, second, and third electrical currents are each at a frequency of approximately 0.67 Hz.

5. The method of claim 1, further comprising adjusting the intensity of one or more of the first, second, and third electrical currents to a patient desired intensity.

6. The method of claim 1, further comprising securing a first output electrode in electrical communication with each of the first and second input electrodes; securing a second output electrode in electrical communication with each of the third and fourth input electrodes; and securing a third output electrode in electrical communication with each of the fifth and sixth input electrodes.

7. The method of claim 6, further comprising securing the first, second, and third output electrodes along a spinal portion of the patient, such that each of the first, second, and third output electrodes are positioned between the corresponding input electrodes.

8. The method of claim 1, wherein securing the third and fourth input electrodes over the left and right suboccipital muscles of the patient comprises securing the third and fourth input electrodes over the left and right Suboccipital Triangles of the patient.

9. The method of claim 1, wherein securing the third and fourth input electrodes over the left and right suboccipital muscles of the patient comprises securing the third and fourth input electrodes over the left and right sternocleidomastoid muscles of the patient.

10. The method of claim 1, wherein securing the third and fourth input electrodes over the left and right suboccipital muscles of the patient comprises securing the third and fourth input electrodes over the left and right rectis muscles of the patient.

11. The method of claim 1, wherein securing the third and fourth input electrodes over the left and right suboccipital muscles of the patient comprises securing the third and fourth input electrodes over the left and right posterior cervicalis muscles of the patient.

12. The method of claim 1, comprising supplying the first, second and third electrical currents simultaneously.

13. A device for performing transcutaneous electrical neural stimulation, the device comprising:
   a power source;
   a first set of electrodes in electrical communication with the power source, the first set of electrodes comprising first and second input electrodes and a first output electrode;
   a second set of electrodes in electrical communication with the power source, the second set of electrodes comprising third and fourth input electrodes and a second output electrode;
   a third set of electrodes in electrical communication with the power source, the third set of electrodes comprising fifth and sixth input electrodes and a third output electrode;
   a current generating mechanism electrically connected to the power source for generating a first electrical current between each of the first and second input electrodes and the first output electrode, for generating a second electrical current between each of the third and fourth input electrodes and the second output electrode, and for generating a third electrical current between each of the fifth and sixth input electrodes and the third output electrode; and
   an amplitude control mechanism for selectively controlling intensity any one or more of the corresponding first, second, and third electrical currents.

14. The device of claim 13, wherein the amplitude control mechanism comprises first, second, and third amplitude control members for separately controlling intensity of the corresponding first, second, and third electrical currents.

15. The device of claim 13, wherein the current generating mechanism is configured to synchronize the frequencies of the first, second, and third electrical currents.

16. The device of claim 13, further comprising a balance control mechanism for selectively adjusting distribution of each of the first, second, and third electrical currents between the input electrodes of the corresponding set of electrodes.

17. The device of claim 16, wherein the balance control mechanism comprises first, second, and third balance control members for separately adjusting distribution of each of the first, second, and third electrical currents between the input electrodes of the corresponding set of electrodes.

18. The device of claim 13, wherein the current generating mechanism is configured to provide the first, second, and third electrical currents at a fixed frequency of approximately 0.67 Hz.

19. The method of claim 1, wherein the first, second, and third electrical currents deliver simultaneous electrical pulses with synchronized frequencies.

20. The method of claim 1, wherein securing the third and fourth electrode over the cervical and suboccipital muscle region comprises positioning to affect the $11^{th}$, 5th and $7^{th}$ cranial nerves.

* * * * *